US011250877B2

(12) United States Patent
Mitchell et al.

(10) Patent No.: US 11,250,877 B2
(45) Date of Patent: Feb. 15, 2022

(54) SOUND DETECTION

(71) Applicant: Audio Analytic Ltd, Cambridgeshire (GB)

(72) Inventors: Christopher Mitchell, Cambridgeshire (GB); Joe Patrick Lynas, Cambridgeshire (GB); Sacha Krstulovic, Cambridgeshire (GB); Amoldas Jasonas, Cambridgeshire (GB); Julian Harris, Cambridgeshire (GB)

(73) Assignee: AUDIO ANALYTIC LTD, Cambridge (GB)

( * ) Notice: Subject to any disclaimer, the term of this patent is extended or adjusted under 35 U.S.C. 154(b) by 180 days.

(21) Appl. No.: 16/521,949

(22) Filed: Jul. 25, 2019

(65) Prior Publication Data
US 2020/0035261 A1    Jan. 30, 2020

(30) Foreign Application Priority Data

Jul. 25, 2018 (GB) ........................................ 1812153

(51) Int. Cl.
*G10L 25/66* (2013.01)
*G06F 16/483* (2019.01)
(Continued)

(52) U.S. Cl.
CPC ............ *G10L 25/66* (2013.01); *A61B 5/7405* (2013.01); *G06F 16/483* (2019.01); *G10L 25/93* (2013.01)

(58) Field of Classification Search
CPC ......... G10L 25/66; G10L 25/90; G10L 25/93; G10L 25/51; G10L 17/08; G10L 15/24;
(Continued)

(56) References Cited

U.S. PATENT DOCUMENTS 6,324,499 B1 * 11/2001 Lewis ..................... G10L 15/26
704/233
2009/0312660 A1    12/2009 Guarino et al.
(Continued)

FOREIGN PATENT DOCUMENTS

WO    2010070314 A1    6/2010
WO    2013142908 A1    10/2013

OTHER PUBLICATIONS

Pramono, et al., "A Cough-Based Algorithm for Automatic Diagnosis of Pertussis" PLOS ONE | DOI:10.1371/journal.pone.0162128 Sep. 1, 2016.
(Continued)

*Primary Examiner* — Huyen X Vo
(74) *Attorney, Agent, or Firm* — Tarolli, Sundheim, Covell & Tummino LLP

(57) ABSTRACT

A method for generating a health indicator for at least one person of a group of people, the method comprising: receiving, at a processor, captured sound, where the captured sound is sound captured from the group of people; comparing the captured sound to a plurality of sound models to detect at least one non-speech sound event in the captured sound, each of the plurality of sound models associated with a respective health-related sound type; determining metadata associated with the at least one non-speech sound event; assigning the at least one non-speech sound event and the metadata to at least one person of the group of people; and outputting a message identifying the at least one non-speech event and the metadata to a health indicator generator module to generate a health indicator for the at least one person to whom the at least one non-speech sound event is assigned.

15 Claims, 3 Drawing Sheets

(51) Int. Cl.
*A61B 5/00* (2006.01)
*G10L 25/93* (2013.01)

(58) Field of Classification Search
CPC ..... G10L 15/02; G06F 16/483; A61B 5/7405; A61B 5/00; A61B 7/00; A61B 5/0823; A61B 5/08; G16H 20/10; G16H 80/00; G16H 50/20
See application file for complete search history.

(56) References Cited

U.S. PATENT DOCUMENTS

| | | | | |
|---|---|---|---|---|
| 2014/0095166 | A1* | 4/2014 | Bell | G10L 19/018 704/270 |
| 2016/0284349 | A1* | 9/2016 | Ravindran | G10L 15/20 |
| 2016/0302003 | A1* | 10/2016 | Rahman | H04R 1/46 |
| 2017/0154638 | A1* | 6/2017 | Hwang | G01S 3/803 |
| 2018/0092603 | A1 | 4/2018 | Duan et al. | |
| 2018/0206764 | A1 | 7/2018 | Ozawa et al. | |
| 2018/0296092 | A1* | 10/2018 | Hassan | G10L 25/66 |
| 2018/0342251 | A1* | 11/2018 | Cohen | G10L 13/08 |
| 2019/0341057 | A1* | 11/2019 | Zhang | G10L 25/78 |

OTHER PUBLICATIONS

Takahashi, et al., "Cough Detection in Spoken Dialogue System for Home Health Care" Fukuoka University, Department of Electronics Engineering and Computer Science, 8-19-1 Nanakuma, Jonan-ku, Fukuoka 814-180, Japan Interspeech 2004—ICSLP, 8th International Conference on Spoken Language Processing, ICC Jeju, Jeju Island, Korea, Oct. 4-8, 2004.
British Search Report for GB1812153.3 dated Jan. 21, 2019.

* cited by examiner

SOUND DETECTION

FIELD OF THE INVENTION

This invention generally relates to identifying sound events as health related and assigning of the sound events to a person.

BACKGROUND

Background information on sound identification systems and methods can be found in the applicant's PCT application WO2010/070314, which is hereby incorporated by reference in its entirety.

The papers "*A Cough-Based Algorithm for Automatic Diagnosis of Pertussis*" (Pramono et al.) and '*Cough Detection in Spoken Dialogue System for Home Health Care*' (Takahashi et al., 8$^{th}$ International Conference on Spoken Language Processing ICC Jeju, Oct. 4-8, 2004; www.isca•speech.org/archive) are directed to detecting non-speech sound events originating from a single person that are related to the person's health.

SUMMARY

The inventors have recognised the potential for new applications of sound identification technology, specifically relating to sound identification systems health and well-being detection.

In particular, the inventors have realised that prior art systems cannot function in an environment where there may be several different health related noises being emitted from several different people. For example, in a care home there may be many different health related noises being emitted by different people. The prior art systems cannot determine/label each of these health related noises and group the noises into clusters, where each cluster corresponds to a person. Rather, the prior art systems are generally concerned merely with specific classification such as, cough classification from a single source, rather than general classification followed by grouping or assigning a number of classified sounds.

There is still a need for a method of detecting health related noises (for example coughs) and grouping these noises to a particular person of a group. None of the prior art addresses a situation where there are noises emitted from more than one person.

According to one aspect of the present disclosure there is provided a method for generating a health indicator for at least one person of a group of people, the method comprising: receiving, at a processor, captured sound, where the captured sound is sound captured from the group of people; comparing the captured sound to a plurality of sound models to detect at least one non-speech sound event in the captured sound, each of the plurality of sound models associated with a respective health-related sound type; determining metadata associated with the at least one non-speech sound event; assigning the at least one non-speech sound event and the metadata to at least one person of the group of people; and outputting a message identifying the at least one non-speech event and the metadata to a health indicator generator module to generate a health indicator for the at least one person to whom the at least one non-speech sound event is assigned.

The metadata may comprise at least one of: a time of the non-speech sound event, a date of the non-speech sound event, a location of the non-speech sound event, and a frequency of occurrence of a health-related sound type.

The assigning may comprise processing the non-speech sound event.

The non-speech sound event may be processed to determine a location estimate of the at least one person, the method further comprising using the location estimate in said assigning.

The assigning may further comprise comparing the location estimate with predetermined location information associated with the at least one person to identify the at least one person.

The method may further comprise: processing the non-speech sound event to determine at least one audio characteristic of the non-speech sound event; and comparing the at least one characteristic to at least one audio characteristic model to identify the at least one person, each of the at least one audio characteristic model associated with a respective human characteristic.

The human characteristic may comprise at least one of age and gender.

The method may further comprise performing speech analysis on speech in the captured sound to identify the at least one person by being referenced in said speech.

The plurality of sound models may comprise at least one sound model associated with a class of a health-related sound type, said comparing thereby identifying the class of one or more of the at least one non-speech sound event, wherein the metadata comprises the class of the one or more non-speech sound event.

The assigning may comprise: calculating a set of acoustic features from the captured sound corresponding to the non-speech sound event; generating an observation vector, $x_n$, for the non-speech sound event, wherein the observation vector $x_n$ comprises at least one of the acoustic features and at least one feature of the metadata, wherein $x_n$ may be a d dimensional vector; for a group of k people, initialising k cluster centroids, $\mu_k$, wherein each cluster centroid may be a d dimensional vector: calculating a cluster label, $c_{(n)}$, for the observation vector $x_n$, wherein $c_{(n)} := \arg\min_k \|x_n - \mu_k\|^2$; calculating a cluster centroid wherein the cluster centroid, $\mu_k$ may be calculated using the equation $$\mu_k := \frac{\sum_{i=1}^{n} 1\{c_{(n)} = k\} x_i}{\sum_{i=1}^{n} 1\{c_{(n)} = k\}}$$

repeating the calculating steps until a convergence state is reached; and assigning the observation vector $x_n$ to the at least one person according to the calculated cluster label $c_{(n)}$.

The method may further comprise: adding the observation vector $x_n$ to an observation set, $S_{obv}$, wherein, the initialisation may be performed by randomly selecting k values from the observation set, $S_{obv}$ and generating each cluster centroid, $\mu_k$, from the randomly selected k values.

The at least one non-speech sound event may comprise one or more of: a cough, a sneeze, a hack, a splutter, a wheeze, a huff, and a moan.

According to another aspect of the present disclosure there is provided a non-transitory computer-readable medium having instructions stored thereon that, when executed by a processor of at least one computing device, causes the at least one computing device to perform any of the above method steps.

According to another aspect of the present disclosure there is provided a sound processing device for generating a health indicator for at least one person of a group of people, wherein the sound processing device comprises a processor configured to: receive, at a processor, captured sound, where the captured sound is sound captured from the group of people using at least one microphone; compare the captured sound to a sound model to determine a sound event type; determine metadata for the sound event, assigning the sound event and the metadata to at least one person; output the sound event and metadata to a health indicator generator module to generate a health indicator for the person to whom the sound event is assigned.

The sound processing device may comprise the health indicator generator module.

The health indicator generator module may be remote to the sound processing device.

These and other aspects will be apparent from the embodiments described in the following. The scope of the present disclosure is not intended to be limited by this summary nor to implementations that necessarily solve any or all of the disadvantages noted.

DETAILED DESCRIPTION

Figure 1:
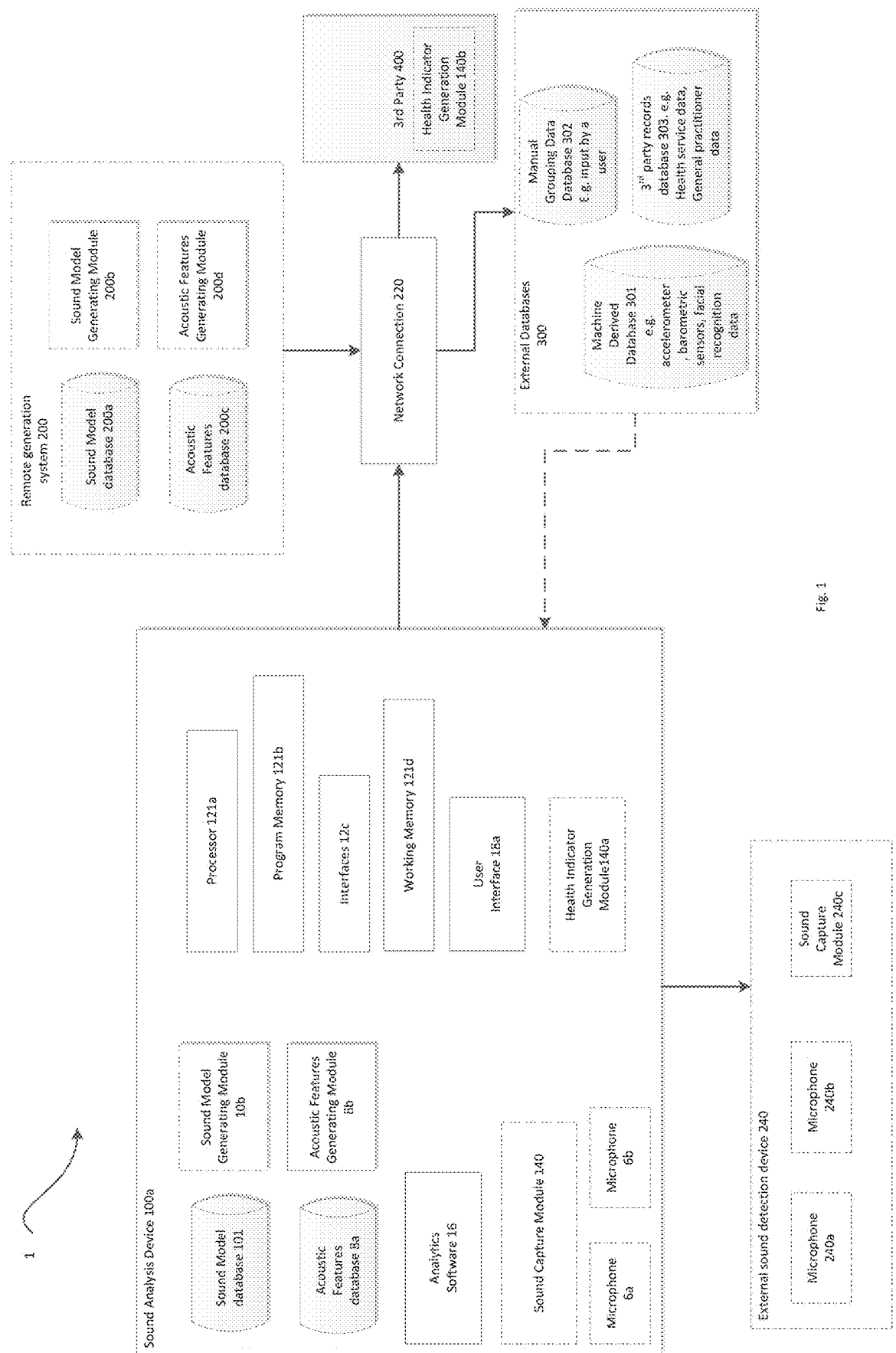
FIG. 1 shows a block diagram of a system for generating a health indicator.

FIG. 1 shows a block diagram of a system 1 for generating a health indicator.

System 1 comprises a sound analysis device 100a, which is in communication with a remote generation system 200, External databases 300 and a 3$^{rd}$ party computing device 400. This connection may be a network connection 220. The sound analysis device 100a may also be in connection with an external sound detection device 240, via a wired or wireless connection.

The sound analysis device 100a may be a PC, a mobile computing device such as a laptop, smartphone, tablet-PC, a server, a consumer electronics device (e.g. a webcam, a smart microphone, etc.) or other electronics device (e.g. a security camera or smart speaker). The device comprises a processor 121a coupled to program memory 121b storing computer program code to implement the sound capture, sound identification and assigning, to working memory 121d and to interfaces 121c such as a screen, one or more buttons, keyboard, mouse, touchscreen, and network interface.

The processor 121a may be an ARM® device. The program memory 121b, in embodiments, stores processor control code to implement functions, including an operating system, various types of wireless and wired interface, storage and import and export from the device.

The sound analysis device 100a is used to receive a sound, identify a health related sound and assign the sound to a person. The sound analysis device 100a outputs information to a health indicator generation (HIG) module 140a, which then generates the health indicator. The information outputted can be a message identifying the a non-speech event and metadata. The HIG module 140a may be on the sound analysis device 100a. The HIG module 140b may be remote to the sound analysis device 100a.

The sound analysis device 100a may comprise one or more microphones (6a, 6b) and a sound capture module 140. The sound capture module receives sound from the microphone(s). At least one microphone (240a, 240b) and a sound capture module (240c) may be part of an external sound detection device 240 which is outside of the sound analysis device 100a. In this case the sound analysis device 100a receives audio data via a connection (wired or wireless) from the external sound detection device 240.

In particular embodiments, the sound analysis device 100a comprises a user interface 18a to enable the user to, for example, assign a sound to a particular person. The user interface 18a may, in other embodiments, be provided via a second device (not shown), or a sound may be automatically assigned to a particular person by the system.

The sound analysis device 100a comprises a sound model database 101 storing a plurality of sound models (or "sound packs"). The sound models may have been previously generated and so are stored on the sound analysis device 100a. Alternatively the device may generate the sound models at sound model generating module 10b. The sound models be used to detect and/or classify a sound type of a non-speech sound event. The sound models stored in the sound model database 101 are each associated with a target health-related sound type (e.g. cough, sneeze etc.). Additionally, for one or more of the health-related sound types, the sound model database 101 may store one or more sound model associated with a class of the health-related sound type. A class is a sub-category of a sound type. A class of cough may be, for example, a wet cough, dry cough or a croup cough. The sound analysis device 100a also comprises analytics software 16 which is used to identify a detected sound, by comparing the detected sound to the sound models (or "sound packs") stored in the sound model database 101.

The sound model database may comprise one or more sound models relating to human characteristics. The human characteristics may be age and/or gender. For example, there may be a sound model associated with a non speech sound event from an infant, a toddler, a teenager, a young adult, an elderly person. Alternatively, or additionally the one or more sound models relating to human characteristics may be associated with a male person and/or a female person.

The sound analysis device 100a may comprise interfaces (18a, 12c), including a user interface 18. The user may or may not be one of persons in the group.

The sound analysis device 100a comprises an acoustic features database 8a which stores acoustic features generated by an acoustic features generating module 8b.

The functionality of the sound analysis device 100a may be implemented in code (e.g. Analytics software 16) stored on a memory (e.g. working memory 121d) comprising one or more storage media, and arranged for execution on the processor 121a comprising on or more processing units. The analytics software 16 is configured so as when fetched from the memory (e.g. 121b) and executed on the processor 121a to perform operations in line with embodiments discussed herein. Alternatively, it is not excluded that some or all of the functionality of the sound analysis device 100a is implemented in dedicated hardware circuitry, or configurable hardware circuitry like an FPGA.

Optionally, external databases 300 are connected to the sound analysis device 100a via a network connection 22, wireless network connection, or via a direct connection. External databases 300 may comprise a Machine Derived Database 301 that contains information from, for example an accelerometer, barometric sensors, facial recognition data. One example of a machine derived database could be an accelerometer in a smart watch. The smart watch could send information to a sound analysis device 100a. The information could be data from an accelerometer which corresponds to the movement of the wearer's (of the smart watch) hands to cover a sneeze. The sound analysis device 100a could incorporate this data from the smart watch in the determination of whether a sneeze has occurred. In this sense data from Machine Derived Database 301 could be used to detect the presence of a sound event, i.e. by alerting the sound analysis device that a sneeze may have happened. The data could further be used to identify the sound. Finally, the information could be used to assign the event to a person, for example, the information could be used to assign the sneeze to the wearer of the smart watch.

One of the external databases 300 may be a Manual Grouping Data Database 302 which comprises data that has been manually input. This data may have been created/inputted by a user of the Manual Grouping Data Database 302 interacting with the Manual Grouping Data Database 302. For example, the Manual Grouping Data Database 302 may ask a user to confirm whether a sound event has been correctly identified, or to confirm whether a sound event has been correctly assigned.

One of the external databases 300 may be a 3rd party records database 303. This could be, for example data stored by a Health service, data from a general practitioner, or general medical statistics/records. This data may be used alongside the outputted message by the HIG module (140a or 140b) to generate a health indicator.

The health indicator, or other information, for example the outputted message or the grouping/assignment, can be output to the 3rd party device 400. This output may be done via network connection, or a wired or wireless connection 220.

Figure 2:
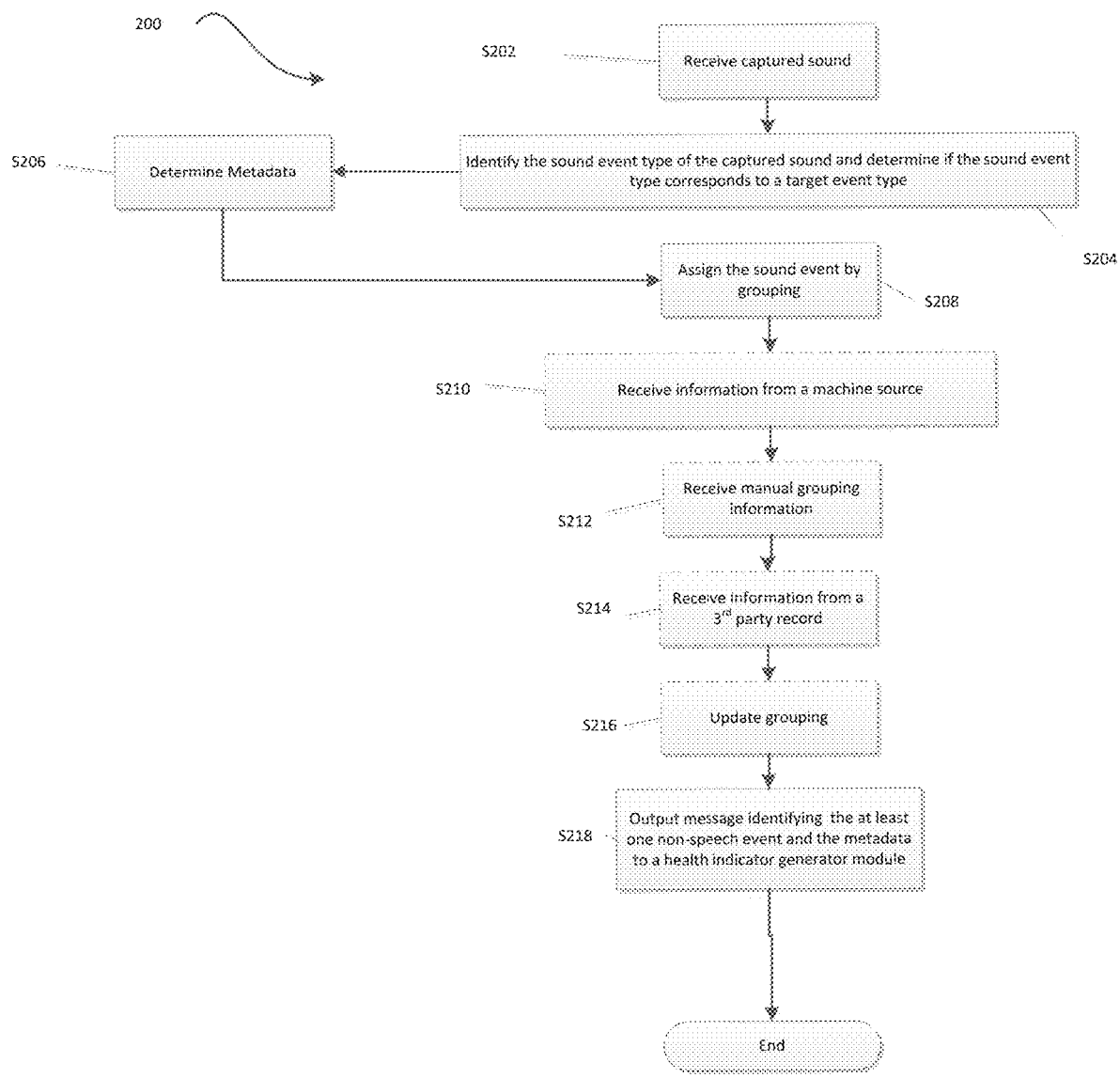
FIG. 2 shows a flow diagram of a method for outputting a message.

FIG. 2 is a flowchart of a process 200 performed by processor 121a. The method may be performed by the sound analysis device 100a of FIG. 1 which may be distributed across multiple devices or installed on a single device.

At S202, audio is received by processor 121a on sound analysis device 100a. The audio may have been captured by (e.g. a microphone) the device or it may be received from outside of the device. The received audio may be continuous ambient/environmental/background audio or could be pre-processed segments of audio.

The processor 121a compares the captured sound to a plurality of sound models, stored in sound model database 101, to detect a non-speech sound event at S204. The sound models may have been previously generated and stored in sound model database 101 on the sound analysis device 100a. The sound models are each associated with a health-related sound type. The sound type may also be referred to as the deep category. The health-related sound type may be, for example, a cough, sneeze, a hack, a splutter, a wheeze, a huff, and a moan. A huff can be described as a laboured or heavy breathing, a deep exhalation of breath. A hack can be described as a loud or persistence cough. A wheeze can be described as a breath with a whistling or rattling sound. The health-related sound type can be determined using sound models and/or acoustic features on processor 121a running analytics software 16.

There are a number of ways a sound model for a captured sound can be generated. The analytics software 16 may use a statistical Markov model for example, where the parameters generated to characterise the captured sound are hidden Markov model (HMM) parameters. Additionally or alternatively, the sound model for a captured sound may be generated using machine learning techniques or predictive modelling techniques such as: neural networks, support vector machine (SVM), decision tree learning, etc.

The applicant's PCT application WO2010/070314, which is incorporated by reference in its entirety, describes in detail various methods to identify sounds. Broadly speaking an input sample sound is processed by decomposition into frequency bands, and optionally de-correlated, for example, using PCA/ICA, and then this data is compared to one or more Markov models to generate log likelihood ratio (LLR) data for the input sound to be identified. A (hard) confidence threshold may then be employed to determine whether or not a sound has been identified; if a "fit" is detected to two or more stored Markov models then preferably the system picks the most probable. A sound is "fitted" to a model by effectively comparing the sound to be identified with expected frequency domain data predicted by the Markov model. False positives are reduced by correcting/updating means and variances in the model based on interference (which includes background) noise.

An example process for detecting a sound using sound models is as follows. A device receives a detected sound, either via its own sound capture module (e.g. a microphone and associated software), or from a separate device. The device initiates audio analytics software 16 stored on the sound analysis device 100a in order to analyse the detected sound. The audio analytics software 16 identifies the detected sound by comparing it to one or more sound models stored within the device in sound model database 101. If the detected sound matches one of the stored sound models, then the sound is identified.

The sound analysis device 100a is preferably configured to detect more than one sound at a time. In this case, the sound analysis device 100a will run two analytics functions simultaneously. An indication of each sound detected and identified is provided to the user.

At S206, metadata is determined from the received audio by processor 121a. This metadata may relate to the date, time, location of the sound event, the frequency of occurrences of the sound/sound event, and the period of the occurrences of the sound event. Alternatively or additionally, the metadata may be generated by processing any of the captured sound itself, for example, the location of the sound event may be determined by using an array of microphones and beam forming.

At S208, the non-speech sound event is assigned to at least one person of the group. The assigning step can be seen as grouping non-speech sound events into one or more clusters, where each cluster is associated with a person. The grouping is separating each of the sound events into different groups depending on properties of the captures sound corresponding to the sound event and/or the metadata. The cluster/group may be linked to an identified person. The assigning at S208 may comprise comparing the captured sound to sound models relating to human characteristics. For example, the assigning may comprise comparing the captured sound to sound models associated with infants, teenagers and young adults. If the teenager model is the best fit with the captured sound, then the information that the captured sound is most likely to be associated with a teenager is used in the assigning step S208.

The metadata may comprise at least one of: a time of the sound event, a date of the sound event, a location of the sound event, and a frequency of occurrence of the sound event type. The sound events may be grouped. The sound event corresponding to the captured sound may be grouped and assigned to a person by processing the sound event type and the metadata. The sound events assigned to the person may be analysed to generate a health indicator for the person.

Each sound event may be assigned to a cluster, a cluster may be associated with a person. The term "cluster" is used herein to refer to one or more non-speech sound events that have been grouped together by way of a grouping process. This process may be referred to as grouping or assigning. It is not necessarily true that each sound event is assigned to a particular identified person (e.g. Bob had twenty coughs on Wednesday afternoon), although this may occur in some embodiments. The sound event may rather be assigned to a cluster where the identity of person associated with the cluster is not known, for example, the names and identities of each of the people may not be known but the number of clusters may still be able to be determined. The cluster may already have other sound events assigned to it. Not every sound event will necessarily be assigned to any cluster. More detail on how sound events are grouped will be described below with reference to FIG. 3. By grouping the sound events, the method is able to generate more detailed information than merely identifying a sound event type. The grouping allows complex, detailed records for each cluster to build up over time. It is also possible to keep track of each cluster over time to determine how the health and wellbeing of the person, who is associated to that cluster, changes over time. It is also possible to determine that a particular person has multiple illnesses because several separate sound events can be assigned to that group/person. It is also possible to track the spread of an illness or disease from one person to another (by analysing clusters). For example, at an initial time a sound event identified as a dry cough is assigned to a first person. At a later time, a sound event identified as a dry cough is assigned to a second person who did not originally have any dry cough sound events assigned to them. It could then be inferred that the first person has infected the second person with the illness/disease causing the dry cough. Generally speaking, the grouping may use machine learning.

The sound analysis device may receive further information from a $3^{rd}$ party (S210, S212, S214). This information could be obtained from what is referred to as a machine source. Machine source data could be data obtained from a sensor or algorithm, for example an accelerometer, barometric sensor, facial recognition data, or any other type of sensor or information obtained and/or processed. For example, the information could be information from speech recognition For example, detection of the words "Bless you John" after a detection of a sneeze sound event count be used to assign the sound event to John. Information could be received from a sensor that is associated with or part of the same device that the sound analysis device may be installed on.

The sound analysis device could receive information relating to grouping that has been inputted manually by a user. The user could be associated with a cluster or they could be a professional who is not associated with any cluster. This grouping information may complement the automated grouping process performed by the sound analysis device.

The $3^{rd}$ party information could be received from a database of $3^{rd}$ party records, such as databases compiled by a health services, general practitioners, or any other professional service associated with health and wellbeing.

Optionally the grouping may be updated (S216) in light of information that may be received from the $3^{rd}$ party.

In S218, a message is output identifying the at least one non-speech event and the metadata to a health indicator generator module (140a, 140b).

The grouping information may be processed in addition to the automated grouping sound analysis device 100a performed by the sound analysis device 100a, and may be used to determine a health indicator(s).

The sound analysis device 100a may analyse at least one of the clusters and may generate a health indicator. Optionally, some of the data obtained from any of the above mentioned $3^{rd}$ parties may be used in the generation of the health indicator. Generally speaking a health indicator will be generated by the health indicator generator module for each cluster, although there could be a health indicator corresponding to more than one cluster.

A health indicator may, for example, be generated by matching clusters and/or more granular individual non speech event types against external databases 300 where external databases are compiled by health professionals who's knowledge of types can indicate underlying health issues.

In one embodiment, the message output at step S218 is received at the health indicator generator module 140a on the sound analysis device 100a and a health indicator is then outputted from the health indicator generator module 140a on the sound analysis device 100a.

In other embodiments, the message output at step S218 is transmitted over network connection 220 to the health indicator generator module 140b on the third party device 400 for use in generating a health indicator by the health indicator generator module 140b. In these embodiments, the health indicator is generated remote to sound analysis device 100a.

The health indicator may be a single score, number or grading representative of a person's health. The health indicator may comprise more data than just a single number, for example, it could be an array, a list, a database, a keyword or a description. The health indicator may be linked to an identified person. The health indicator may give some indication regarding a general or particular aspect of a person's health and/or wellbeing.

The indicator may be used to alert $3^{rd}$ parties, for instance in case of an emergency, such as a fall. The indicator may be used to alert a $3^{rd}$ party that a person's symptoms have changed and/or have got more severe. The $3^{rd}$ party may then act on this information.

The health indicator may be output to a device that has a UI, for example, to another device associated with one of the people of the group. For example, the sound analysis device 100a may communicate with a device that reminds a person to take medication. More generally speaking, this device could be a medical related device which can provide an interface to a user in order to provide information regarding actions or information as a result of the health indicator. Similarly, the health indicator may be output to a human that can interact with a person associated with the cluster, in this regard, rather than a device interacting reminding a person to take medication, a health professional may remind the person to take medication. The health indicator may be outputted to a health professional not only to perform an action but also for the health professional add the indicator to a record already held by the health professional. In this way the health indicator may complement health records already maintained by a $3^{rd}$ party (who may be a health professional).

The health indicator may be output to a digital virtual assistant, including a voice assistant. The outputting of the health indicator may cause the assistant to perform certain tasks including interacting with the user, contacting other people (e.g. health professionals) or scheduling appointments.

The health indicator may be output to a $3^{rd}$ party that uses the indicator in relation to context based advertisements. The health indicator could be used by such services to provide advertisements that are targeted/related to any health issues associated with the health indicator. For example, the health indicators may indicate that a first person has a dry cough and a second person has a chest infection. The context based advertising could then advertise cough related medicine to the first person, and health services related to a chest infection for the second person. The health indicator(s) may also comprise an indication that the first and second person are in contact with one another. This may allow the context based advertisement to recommend products to the second person that are designed to boost the immune system and therefore lower the chance of the first person infecting the second person.

Figure 3:
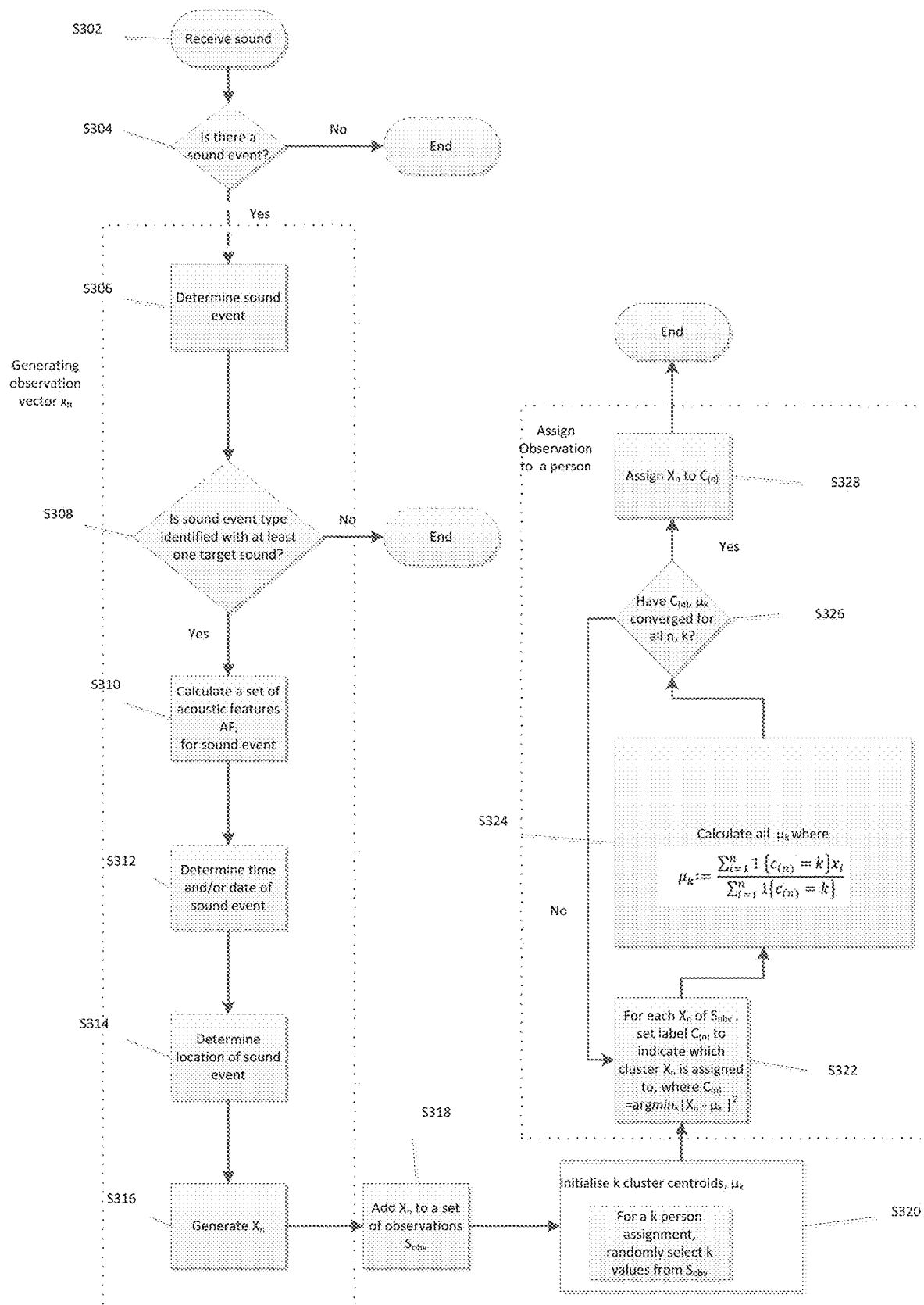
FIG. 3 shows a flow diagram of a method for assigning a sound event to a person.

FIG. 3 is a flowchart of a process 200 performed by processor 121a.

At S302, audio is received by a processor 121a on sound analytics device 100a. The audio may have been captured by (e.g. a microphone) the device or it may be received from outside of the device. The received audio may be continuous ambient/environmental/background audio or could be pre-processed segments of audio.

Optionally, at S304, it is determined by the processor 121a running analytic software 16, if there is a sound event associated with the received sound. If there is no sound event the process ends, and the sound analysis device 100a may continue to monitor for sound events in other portions of received sound. This may be a continuous process, where the sound analysis device 100a is monitoring a continuous stream of background/environmental sound for sound events. Advantageously, this monitoring process may be done with minimal power, so that the sound analysis device 100a can conserve power. Therefore the processor 121a of the sound analysis device 100a can reside in a low power state, and only boot up to higher power states if a sound event is determined to have taken place.

In S306-308, if a sound event is determined to have occurred, the processor 121a determines the sound event type. For example, the sound event type may be a cough, sneeze, an impact. Determining the sound event type may be done using a sound recognition system which may be part of the sound analysis device 100a.

Optionally, in S308, if the sound event type is not a target health-related sound type then the process ends. For example, the processor 121a running analytic software 16 may be configured to process/assign only cough sounds. Therefore, if it is determined that the sound event type is a sneeze, the process ends. This advantageously means that the following steps (i.e. assigning) are not performed for sound event types that the sound analysis device 100a is not configured to monitor (determine and assign/group). This has energy/power saving benefits because it reduces the amount of unnecessary processing.

At S310, a set of acoustic features is calculated for a sound event. This may occur in response to the determination that the sound event type is a target sound event type, or it may be done regardless. An observation vector, $X_n$ is generated comprising at least one of the acoustic features. The observation vector is a d dimensional vector An example of an acoustic features is the fundamental frequency of the captured sound, which can be defined as the lowest frequency of a periodic waveform. The fundamental frequency could also be the lowest frequency wave in a Fourier series representation of the captured sound. Another example acoustic feature is the tonality of the captured sound, which may be described as the spread of sound energy across the sound spectrum. Another example acoustic feature is the loudness of the sound. The captured sound may be processed to generate at least one acoustic feature.

The time and date of the sound event may be determined at S312. The location of the sound event may be determined at S314. This may be determined by beam forming using an array of microphones. Movement of the source of the non-speech sound event may also be determined for example, using beam forming. Optionally, external devices and/or sensors may be used in the any of steps S310 to S316, for example accelerometers worn by one person of the group of people could be used to determine movement of the source of a non-speech sound event. As another example, location tracking information as captured by, for example a mobile telephone, could be used in the determination of the location of the sound event. The duration of time of the sound event may be determined. The frequency of times the sound event type occurs may be determined. If the sound event occurs more than once, a period of the occurrence of the sound event can be determined. The generated observation vector may further comprise any of these determined values. The observation vector may comprise acoustic features, and optionally time/date/location of the sound event.

The observation vector is added to a set of observations, which may comprise other observation vectors that have been previously added to the set. Where there are k people in the group, k cluster centroids are initialised. In some embodiments, the value of k is unknown, in other words, it is not known how many people are in the group. In this scenario, the numerical value of k can be resolved using techniques known to persons skilled in the art. Each cluster centroid may be a d dimensional vector in the same space as the observation vector(s). Random values from the observation vectors of the set of observations may be used to initialise the cluster centroids.

For each observation vector of the set of observations, a label is set to indicate which cluster the observation vector belongs to. The label may be determined by the equation $$c_{(n)} := \arg\min_k \|x_n - \mu_k\|^2$$

where n is the number of the observation, $c_{(n)}$ is the label of the nth observation to indicate which cluster it is part of, where $\|x-\mu\|$ means Euclidean distance between vectors x and $\mu$.

Using the cluster label(s) $c_{(n)}$, cluster centroids are calculated. For example, the cluster centroids may be determined using the equation $$\mu_k := \frac{\sum_{i=1}^{n} 1\{c_{(n)} = k\} x_i}{\sum_{i=1}^{n} 1\{c_{(n)} = k\}}$$

The results for each of the k cluster centroids, $\mu_k$, are fed back into the equation for $c_{(n)}$. These series of equations are repeated until convergence. The end result will be k number of cluster centroids, and also a label for each observation vector assigning the observation vectors to a cluster centroid. The convergence state is when the repeated values of each cluster centroid value differ by a minimal amount that is deemed to be within a level of agreement. The convergence state for each of the cluster labels is similarly when subsequently calculated values of the cluster labels differ by a minimal amount deemed to be within a level of agreement.

Below is described a technique for assigning sound occurrence types to k-people in relation to a specific devices location and time of occurrence.

Below is an example of how sound type occurrences (sneezes, coughs, nose blows etc.) can be clustered so as to assign sound occurrences of specific types to k persons. Note, other methods of assignment could also be used. Once assigned further analysis can be conducted to determine the appropriate action e.g. person 1 has been coughing and blowing their nose a lot over the last two weeks and person 2 has started to cough and sneeze more than usual in the last two days so has probably contracted person 1's cold.

Given a set of observations $(x_1, x_2, \ldots, x_n)$ where each observation is a d-dimensional real vector calculated when a specific sound type is detected. The observation vector is made up of:

$$x_n = (AF_1, AF_2, \ldots, AF_i, pos_x, pos_y, pos_z, \text{day}, \text{hour})$$

Where $AF_i$ is a number of acoustic features (calculations made on the audio stream e.g. fundamental frequency, harmonicity, estimated vocal track length) calculated from the audio that has been identified as containing at least one of the target sound types (e.g. coughing, sneezing, blowing of the nose) recognised by a sound recognition system, $pos_x$, $pos_y$, $pos_z$ is the estimated location of the sound source in meters (a suitable alternative to a Euclidean geometry could also be used), this can be derived from a microphone array using beam forming techniques or from other sources, the day would be a whole number drawn from the following interval 1≤day≤7 representing the seven days of the week, the hour is the whole number drawn from the following internal 1≤hour≤24 representing the 24 hours in the day. Note, more granular and other methods of representations of time can be used.

To calculate the k person assignment of the observations first initialise the cluster centroids $\mu_1, \mu_2, \ldots, \mu_k \in \mathbb{R}^d$ where each cluster centroid is a d-dimensional real vector from the same space as the observations. Random initialisation each of the k cluster centroids by randomly selecting k values from the observation vectors. Note, other methods of initialisation could be used.

To assign an observation to a person cluster repeat the following steps until convergence is reached:

Step 1: For every observation n, set the label c to indicate which cluster it is part of, where $\|x-\mu\|$ means Euclidean distance between vectors x and $\mu$.

$$c_{(n)} := \arg\min_k \|x_n - \mu_k\|^2$$

Step 2: For every cluster centroid (the k persons)

$$\mu_k := \frac{\sum_{i=1}^{n} 1\{c_{(n)} = k\} x_i}{\sum_{i=1}^{n} 1\{c_{(n)} = k\}}$$

Once convergence has been reached the observation vector labels c can be used to determine which person id or cluster the sound type occurrence can be assigned to and further statistical analysis and meaning conducted. Note, there are methods known to a suitable individual skilled in the area for estimating the appropriate number of clusters that should be used to represent a set of observations if they are not known a priori by removing or adding cluster centroids in the steps above. These techniques are not covered here.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A method for generating a health indicator for at least one person of a group of people, the method comprising:
    receiving, at a processor, captured sound, where the captured sound is sound captured from the group of people;
    comparing the captured sound to a plurality of sound models, each of the plurality of sound models associated with a respective health-related sound type;
    detecting at least one non-speech sound event in the captured sound based on the comparing;
    determining metadata associated with the at least one non-speech sound event;
    assigning the at least one non-speech sound event to at least one person of the group of people by processing the metadata, wherein the assigning comprises:
        calculating a set of acoustic features from the captured sound corresponding to the non-speech sound event;
        generating an observation vector, $x_n$, for the non-speech sound event, wherein the observation vector $x_n$ comprises at least one of the acoustic features and at least one feature of the metadata, wherein $x_n$ is a d dimensional vector;
        for a group of k people, initialising k cluster centroids, $\mu_k$, wherein each cluster centroid is a d dimensional vector,
        calculating a cluster label, $c_{(n)}$, for the observation vector $x_n$, wherein $c_{(n)} := \arg\min_k \|x_n - \mu_k\|^2$;
        calculating a cluster centroid wherein the cluster centroid, $\mu_k$ is calculated using the equation:

$$\mu_k := \frac{\sum_{i=1}^{n} 1\{c_{(n)} = k\} x_i}{\sum_{i=1}^{n} 1\{c_{(n)} = k\}};$$

repeating the calculating steps until a convergence state is reached; and
        assigning the observation vector $x_n$ to the at least one person according to the calculated cluster label $c_{(n)}$; and
    outputting a message identifying the at least one non-speech event and the metadata to a health indicator generator module to generate a health indicator for the at least one person of the group of people to whom the at least one non-speech sound event is assigned.

2. The method of claim 1, wherein the metadata comprises at least one of: a time of the non-speech sound event, a date of the non-speech sound event, a location of the non-speech sound event, and a frequency of occurrence of a health-related sound type.

3. The method of claim 1, wherein the assigning comprises processing the non-speech sound event.

4. The method of claim 3, wherein the non-speech sound event is processed to determine a location estimate of the at least one person, the method further comprising using the location estimate in said assigning.

5. The method of claim 4, said assigning further comprising comparing the location estimate with predetermined location information associated with the at least one person to identify the at least one person.

6. The method of claim 3, further comprising:
processing the non-speech sound event to determine at least one audio characteristic of the non-speech sound event; and
comparing the at least one audio characteristic to at least one audio characteristic model to identify the at least one person, each of the at least one audio characteristic model associated with a respective human characteristic.

7. The method of claim 6, wherein the human characteristic comprises at least one of: age and gender.

8. The method of claim 1, wherein the method further comprises performing speech analysis on speech in the captured sound to identify the at least one person by being referenced in said speech.

9. The method of claim 1, wherein the plurality of sound models comprise at least one sound model associated with a class of a health-related sound type, said comparing thereby identifying the class of one or more of the at least one non-speech sound event, wherein the metadata comprises the class of the one or more non-speech sound event.

10. The method of claim 1, further comprising:
adding the observation vector $x_n$ to an observation set, $S_{obv}$,
wherein, the initialisation is performed by randomly selecting k values from the observation set, $S_{obv}$ and generating each cluster centroid, $\mu_k$, from the randomly selected k values.

11. The method of claim 1, wherein the at least one non-speech sound event comprises one or more of: a cough, a sneeze, a hack, a splutter, a wheeze, a huff, and a moan.

12. A non-transitory computer-readable medium having instructions stored thereon that, when executed by a processor of at least one computing device, causes the at least one computing device to:
receive captured sound, where the captured sound is sound captured from a group of people;
compare the captured sound to a plurality of sound models, each of the plurality of sound models associated with a respective health-related sound type;
detect at least one non-speech sound event in the captured sound based on the comparison;
determine metadata associated with the at least one non-speech sound event;
assign the at least one non-speech sound event to at least one person of the group of people by processing the metadata, wherein the assigning comprises:
calculating a set of acoustic features from the captured sound corresponding to the non-speech sound event;
generating an observation vector, $x_n$, for the non-speech sound event, wherein the observation vector $x_n$ comprises at least one of the acoustic features and at least one feature of the metadata, wherein $x_n$ is a d dimensional vector;
for a group of k people, initialising k cluster centroids, $\mu_k$, wherein each cluster centroid is a d dimensional vector,
calculating a cluster label, $c_{(n)}$, for the observation vector $x_n$, wherein $c_{(n)}:=\arg\min_k \|x_n - \mu_k\|^2$;
calculating a cluster centroid wherein the cluster centroid, $\mu_k$ is calculated using the equation:

$$\mu_k := \frac{\sum_{i=1}^{n} 1\{c_{(n)} = k\} x_i}{\sum_{i=1}^{n} 1\{c_{(n)} = k\}};$$

repeating the calculating steps until a convergence state is reached; and
assigning the observation vector $x_n$ to the at least one person according to the calculated cluster label $c_{(n)}$; and
output a message identifying the at least one non-speech event and the metadata to a health indicator generator module to generate a health indicator for the at least one person of the group of people to whom the at least one non-speech sound event is assigned.

13. A sound processing device for generating a health indicator for at least one person of a group of people, wherein the sound processing device comprises a processor configured to:
receive, at the processor, captured sound, where the captured sound is sound captured from the group of people using at least one microphone;
compare the captured sound to a plurality of sound models, each of the plurality of sound models associated with a respective health-related sound type;
detect at least one non-speech sound event in the captured sound based on the comparison;
determine metadata associated with the at least one non-speech sound event;
assign the at least one non-speech sound event to at least one person of the group of people by processing the metadata, wherein the assigning comprises:
calculating a set of acoustic features from the captured sound corresponding to the non-speech sound event;
generating an observation vector, $x_n$, for the non-speech sound event, wherein the observation vector $x_n$ comprises at least one of the acoustic features and at least one feature of the metadata, wherein $x_n$ is a d dimensional vector;
for a group of k people, initialising k cluster centroids, $\mu_k$, wherein each cluster centroid is a d dimensional vector,
calculating a cluster label, $c_{(n)}$, for the observation vector $x_n$, wherein $c_{(n)}:=\arg\min_k \|x_n - \mu_k\|^2$;
calculating a cluster centroid wherein the cluster centroid, $\mu_k$ is calculated using the equation $$\mu_k := \frac{\sum_{i=1}^{n} 1\{c_{(n)} = k\} x_i}{\sum_{i=1}^{n} 1\{c_{(n)} = k\}};$$

repeating the calculating steps until a convergence state is reached; and
assigning the observation vector $x_n$ to the at least one person according to the calculated cluster label $c_{(n)}$; and
output a message identifying the at least one sound event and the metadata to a health indicator generator module to generate a health indicator for the at least one person of the group of people to whom the sound event is assigned.

14. The sound processing device of claim 13 wherein the sound processing device comprises the health indicator generator module.

15. The sound processing device of claim 13 wherein the health indicator generator module is remote to the sound processing device.

\* \* \* \* \*

UNITED STATES PATENT AND TRADEMARK OFFICE
CERTIFICATE OF CORRECTION

| | |
|---|---|
| PATENT NO. | : 11,250,877 B2 |
| APPLICATION NO. | : 16/521949 |
| DATED | : February 15, 2022 |
| INVENTOR(S) | : Mitchell et al. |

It is certified that error appears in the above-identified patent and that said Letters Patent is hereby corrected as shown below:

On the Title Page

Column 1, Item (72) Inventors:
Reads "Amoldas Jasonas, Cambridgeshire (GB)"

Should read:
--Arnoldas Jasonas, Cambridgeshire (GB)--

Signed and Sealed this
Third Day of May, 2022

Katherine Kelly Vidal
*Director of the United States Patent and Trademark Office*